(12) United States Patent
Druzgala et al.

(10) Patent No.: US 7,145,020 B2
(45) Date of Patent: *Dec. 5, 2006

(54) MATERIALS AND METHODS FOR TREATING COAGULATION DISORDERS

(75) Inventors: Pascal Druzgala, Santa Rosa, CA (US); Xiaoming Zhang, Campbell, CA (US); Jurg R. Pfiste, Los Altos, CA (US)

(73) Assignee: Aryx Therapeutics, Fremont, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 10/822,129

(22) Filed: Apr. 8, 2004

(65) Prior Publication Data

US 2004/0220258 A1    Nov. 4, 2004

Related U.S. Application Data

(63) Continuation-in-part of application No. 10/132,750, filed on Apr. 24, 2002, now Pat. No. 6,864,279.

(60) Provisional application No. 60/286,079, filed on Apr. 24, 2001.

(51) Int. Cl.
*C07D 311/02* (2006.01)
(52) U.S. Cl. ............................ 549/285; 549/305
(58) Field of Classification Search ................ 549/285, 549/305; 514/465, 457
See application file for complete search history.

(56) References Cited

U.S. PATENT DOCUMENTS

| 3,325,515 | A | * | 6/1967 | Schmitt et al. ............. 549/282 |
| 4,748,185 | A | | 5/1988 | Entwistle et al. |
| 5,510,375 | A | | 4/1996 | Domagala et al. |
| 5,686,486 | A | | 11/1997 | Tomich et al. |
| 5,856,525 | A | | 1/1999 | Li et al. |

FOREIGN PATENT DOCUMENTS

| FR | 2765579 A1 | 1/1999 |
| GB | 1024383 | 3/1966 |
| GB | 1032253 | 6/1966 |

OTHER PUBLICATIONS

Ciliag Ltd 'Disubstituted nicotinamides' CA 51:5827 (1957).*

Zhao, H et al 'Coumarin-based inhibitors of HIV integrase' J. Med. Chem, 1997, 40, 242-249.*

Poetzsch, B et al 'Monitoring of recombinant hirudin: assessment of a plasma-based ecarin clotting time assy' CA 127:130379 (1997).*

Ruan, Z et al 'Study of sulfated beta-cyclodextrin chiral additive for enantiomeric separation by capillary electrophoresis' CA 131:303449 (1999).*

Avetisyan, AA et al 'Synthisis and certain conversions of 3-(3,3-dichloroallyl)-4-hydroxycoumarin' CA 128:48113 (1997).*

Schmitt, J et al 'Synthesis of a new anticoagulant' CA 66:115544 (1967).*

Masubuchi M et al 'beta-(4-hydroxy-3-coumarinyl)-beta-substituted propionate' CA 59:75249 (1963).*

Morgan, LH et al 'High throughput method for measuring physiochemical values using pH gradients and affinity chromatog. stationary phases' CA 133:55643 (2000).*

Sullivan, WR et al 'hydroxycoumarins. II. the condesation of aldehydes with 4-hydroxycoumarins' CA 38:5011 (1944).*

Schmitt, J. et al. "Sur un nouvel st puissant anticoagulant de sythese," *Chemie Therapeutique* (1966), vol. 1, pp. 301-304. (In French, translation also included).

Svetlik, Jan et al. "Expedient Synthesis of 3-Arylpropionic Acid Derivatives," *Synthetic Communications* (1993), vol. 23, No. 5, pp. 631-640.

Thaisrivongs, Suvit et al. "Structure-based Design of Novel HIV Inhibitors: Carboxamide-Containing 4-Hydroxycoumarins and 4-Hydrozy-2-pyrones as Potent Nonpeptidic Inhibitors," *J. Med. Chem.* (1995), vol. 38, pp. 3624-3637.

Zhao, H. et al. "Coumarin-based inhibitors of HIV Integrase," *J. Med. Chem.* (1997), vol. 40, pp. 242-249.

* cited by examiner

*Primary Examiner*—Amelia A. Owens
(74) *Attorney, Agent, or Firm*—McDonnell Boehnen Hulbert & Berghoff LLP

(57) ABSTRACT

This invention is drawn to compounds which are more easily metabolized by the metabolic drug detoxification systems. Particularly, warfarin analogs which have been designed to include esters within the structure of the compounds are taught. The invention teaches methods of reducing the toxicity of drugs comprising the introduction of ester groups into drugs during the synthesis of the drug. This invention is also drawn to methods of treating coagulation disorders comprising the administration of compounds which have been designed to be metabolized by serum or intracellular hydrolases and esterases. Pharmaceutical compositions of the ester containing warfarin, analogs are also taught.

12 Claims, No Drawings

MATERIALS AND METHODS FOR TREATING COAGULATION DISORDERS

CROSS-REFERENCE TO RELATED APPLICATION(S)

This application is a continuation-in-part of U.S. application Ser. No. 10/132,750, filed Apr. 24, 2002; now U.S. Pat. No. 6,864,279 which claims the benefit of U.S. Provisional Application No. 60/286,079, filed Apr. 24, 2001.

BACKGROUND OF INVENTION

Warfarin (coumarin) is an anticoagulant which acts by inhibiting vitamin K -dependent coagulation factors. Warfarin based compounds are, typically, derivatives of 4-hydroxycoumarin, such as 3-(a-acetonylbenzyl)-4-hydroxycoumarin (COUMADIN). COUMADIN and other coumarin anticoagulants inhibit the synthesis of vitamin K dependent clotting factors, which include Factors II, VII, IX and X. Anticoagulant proteins C and S are also inhibited by warfarin anticoagulants. Warfarin is believed to interfere with clotting factor synthesis by inhibiting vitamin $K_1$ epoxide regeneration.

An anticoagulation effect is generally seen about 24 hours after administration and single doses of warfarin are effective for 2 to 5 days. While anticoagulants have no direct effect on an established thrombus and do not reverse ischemic tissue damage, anticoagulant treatment is intended to prevent the extension of formed clots and/or to prevent secondary thromboembolic complications. These complications may result in serious and possibly fatal sequelae.

Warfarin is typically used for the treatment of in patients suffering from atrial fibrillation. Such treatment reduces the incidence of systemic thromboembolism and stroke. The FDA has approved warfarin for the following indications: 1) the treatment or prophylaxis of venous thrombosis and pulmonary embolism, 2) thromboembolic complications associated with atrial fibrillation and/or cardiac valve replacement, and 3) reducing the risk of death, recurring myocardial infarction, and stroke or systemic embolism after myocardial infarction.

A number of adverse effects are associated with the administration of warfarin. These include fatal or nonfatal hemorrhage from any tissue or organ and hemorrhagic complications such as paralysis. Other adverse effects include paresthesia, headache, chest abdomen, joint, muscle or other pain, dizziness, shortness of breath, difficult breathing or swallowing, unexplained swelling, weakness, hypotension, or unexplained shock. Other adverse reactions reported include hypersensitivity/allergic reactions, systemic cholesterol microembolization, purple toes syndrome, hepatitis, cholestatic hepatic injury, jaundice, elevated liver enzymes, vasculitis, edema, fever, rash, dermatitis, including bullous eruptions, urticaria, abdominal pain including cramping, flatulence/bloating, fatigue, lethargy, malaise, asthenia, nausea, vomiting, diarrhea, pain, headache, dizziness, taste perversion, pruritus, alopecia, cold intolerance, and paresthesia including feeling cold and chills.

Drug toxicity is an important consideration in the treatment of humans and animals. Toxic side effects resulting from the administration of drugs include a variety of conditions which range from low grade fever to death. Drug therapy is justified only when the benefits of the treatment protocol outweigh the potential risks associated with the treatment. The factors balanced by the practitioner include the qualitative and quantitative impact of the drug to be used as well as the resulting outcome if the drug is not provided to the individual. Other factors considered include the physical condition of the patient, the disease stage and its history of progression, and any known adverse effects associated with a drug.

It is important to note that drug toxicity is an important consideration in the treatment of individuals. Toxic side effects resulting from the administration of drugs include a variety of conditions which range from low grade fever to death. Drug therapy is justified only when the benefits of the treatment protocol outweigh the potential risks associated with the treatment. The factors balanced by the practitioner include the qualitative and quantitative impact of the drug to be used as well as the resulting outcome if the drug is not provided to the individual. Other factors considered include the clinical knowledge of the patient, the disease and its history of progression, and any known adverse effects associated with a drug.

Drug elimination is the result of metabolic activity upon the drug and the subsequent excretion of the drug from the body. Metabolic activity can take place within the vascular supply and/or within cellular compartments or organs. The liver is a principal site of drug metabolism. The metabolic process can be broken down into synthetic and nonsynthetic reactions. In nonsynthetic reactions, the drug is chemically altered by oxidation, reduction, hydrolysis, or any combination of the aforementioned processes. These processes are collectively referred to as Phase I reactions.

In Phase II reactions, also known as synthetic reactions or conjugations, the parent drug, or intermediate metabolites thereof, are combined with endogenous substrates to yield an addition or conjugation product. Metabolites formed in synthetic reactions are, typically, more polar and biologically inactive. As a result, these metabolites are more easily excreted via the kidneys (in urine) or the liver (in bile). Synthetic reactions include glucuronidation, amino acid conjugation, acetylation, sulfoconjugation, and methylation.

Drug therapy using warfarin is particularly difficult because the metabolism of warfarin is complex and subject to interactions with a host of other drugs, including drugs that are commonly prescribed in patients suffering from atrial fibrillation, such as amiodarone for example. Warfarin is a mixture of enantiomers having different intrinsic activities at the vitamin K epoxide reductase (VKER) enzyme. These enantiomers have different metabolic pathways using different CYP450 isozymes. The CYP450 metabolic system is highly inducible or repressible by a host of external factors such as diet and other medications. Also, the CYP450 system is subject to many genetic variations and has a low capacity and is easily saturable. For these reasons the metabolism of warfarin is subject to unpredictable variations and each enantiomer has a different metabolic fate and different potencies at the VKER enzyme.

In addition, warfarin activity at the VKER enzyme results in inhibition of coagulation factors II, VII, IX, and X, which have different half-lives of their own, ranging from hours (factor VII) to days (factor X). Because of this complex situation, the pharmacological effect (increased coagulation time) of warfarin becomes apparent only 5 to 10 days after a dose. It is therefore easy to understand why warfarin therapy is extremely difficult to predict and why patients are at high risk of bleeding complications including death. In the current state of warfarin therapy, patients on warfarin must report to a coagulation lab once a week in order to be monitored and in order to detect any early risk of bleeding complications. Even with this strict monitoring system, many patients on warfarin die every year from bleeding complications.

The potential clinical problems and business risk associated with developing drugs, which must past through the P450 metabolism "gauntlet", is markedly increased in the United States by the following two facts: 1) the number of prescriptions filled in this country has increased to about 3 billion per year or 10 per person, and 2) patients, particularly those that live longer and have more complex medical problems, tend to take multiple medications. The latter issue is important because the incidence of ADRs rises exponentially when subjects take more than four drugs. Although it is good practice to avoid polypharmacy, in many cases this is not possible because patients require different classes of drugs to effectively treat complex medical conditions.

The landscape of drug R&D is littered by failed drugs that were withdrawn by the FDA because they caused fatal ADRs involving CYP metabolism. These drugs were clinically effective and in many cases commercially successful. Notable drugs that were withdrawn due to ADR-related deaths involving CYP450 metabolism include terfenadine (February 1998), astemizole (July 1999) and cisapride (January 2000). In each of these cases, drug interactions involving CYP3A4 caused concentrations of the pharmaceutical agent to increase to such a degree that it significantly inhibited a particular type of potassium channel in the heart called $I_{Kr}$, which in turn, prolonged the QT interval and caused a potentially fatal form of ventricular tachyarrhythmia called torsades de pointes.

A warfarin analog that has a controllable and a predictable metabolic fate, not depending on CYP450, is therefore highly desirable and would be an important addition to the armamentarium of drugs available for treating atrial fibrillation patients.

BRIEF SUMMARY

The subject invention provides materials and methods for safe and effective anticoagulant treatment. In a preferred embodiment, the subject invention provides therapeutic anticoagulant compounds. The compounds of the subject invention can be used to treat at-risk populations thereby bringing relief of symptoms, improving the quality of life, preventing acute and long-term complications, reducing mortality and treating accompanying disorders.

Advantageously, the subject invention provides compounds which are readily metabolized by the physiological metabolic drug detoxification systems. Specifically, in a preferred embodiment, the therapeutic compounds of the subject invention contain an ester group, which does not detract from the ability of these compounds to provide a therapeutic benefit, but which makes these compounds more susceptible to degradation by hydrolases, particularly serum and/or cytosolic esterases. The subject invention further provides methods of treatment comprising the administration of these compounds to individuals in need of anticoagulant treatment.

In a further embodiment, the subject invention pertains to the breakdown products which are formed when the therapeutic compounds of the subject invention are acted upon by esterases. These breakdown products can be used as described herein to monitor the clearance of the therapeutic compounds from a patient.

In yet a further embodiment, the subject invention provides methods for synthesizing the therapeutic compounds of the subject invention.

The subject invention provides materials and methods for the treatment of coagulation disorders. Specifically, the subject invention provides compounds which are readily metabolized by the metabolic drug detoxification systems. Specifically, this invention provides compounds which are susceptible to degradation by hydrolases, particularly serum and/or cytosolic esterases. This invention is also drawn to methods of treating coagulation disorders.

This invention is drawn to compounds which are more easily metabolized by the metabolic drug detoxification systems. This invention is also drawn to methods of treating coagulation disorders. Specifically, this invention provides analogs of drugs which have been designed to be more susceptible to degradation by hydrolases, particularly serum and/or cytosolic esterases and methods of treatment comprising the administration of these analogs to individuals.

DETAILED DISCLOSURE

The subject invention provides materials and methods for anticoagulant treatment. Advantageously, the therapeutic compounds of the subject invention are stable in storage but have a shorter half-life in the physiological environment than other drugs which are available for anticoagulant treatment; therefore, the compounds of the subject invention can be used with a lower incidence of side effects and toxicity.

In a preferred embodiment of the subject invention, therapeutic compounds are provided which are useful in providing anticoagulant treatment and which contain an ester group that is acted upon by esterases thereby breaking down the compound and facilitating its efficient removal from the treated individual. In a preferred embodiment the therapeutic compounds are metabolized by the Phase I drug detoxification system.

A further aspect of the subject invention pertains to the breakdown products that are produced when the therapeutic compounds of the subject invention are acted upon by esterases. The presence of these breakdown products in the urine or serum can be used to monitor the rate of clearance of the therapeutic compound from a patient.

The subject invention further provides methods of synthesizing the unique and advantageous therapeutic compounds of the subject invention. Particularly, methods of producing less toxic therapeutic agents comprising introducing ester groups into therapeutic agents (target drugs) are taught. The ester linkage may be introduced into the compound at a site that is convenient in the manufacturing process for the target drug. Additionally, the sensitivity of the ester linkage may be manipulated by the addition of side groups which hinder or promote the hydrolytic activity of the hydrolases or esterases responsible for cleaving the drug at the ester locus. Methods of adding such side groups, as well as the side groups themselves, are well known to the skilled artisan and can be readily carried out utilizing the guidance provided herein.

The subject invention further provides anticoagulant treatment comprising the administration of a therapeutically effective amount of esterified coumarin analogs to an individual in need of treatment. Accordingly, the subject invention provides esterified coumarin analogs and pharmaceutical compositions of these esterified compounds. In a preferred embodiment the patient is a human; however, animals also can be treated.

Adverse drug-drug interactions (DDI), elevation of liver function test (LFT) values, and QT prolongation leading to torsades de pointes (TDP) are three major reasons why drug candidates fail to obtain FDA approval. All these causes are, to some extent metabolism-based. A drug that has two metabolic pathways, one oxidative and one non-oxidative, built into its structure is highly desirable in the pharmaceutical industry. An alternate, non-oxidative metabolic pathway provides the treated subject with an alternative drug detoxification pathway (an escape route) when one of the oxidative metabolic pathways becomes saturated or non-functional. While a dual metabolic pathway is necessary in order to provide an escape metabolic route, other features are needed to obtain drugs that are safe regarding DDI, TDP, and LFT elevations.

In addition to having two metabolic pathways, the drug should have a rapid metabolic clearance (short metabolic half-life) so that blood levels of unbound drug do not rise to dangerous levels in cases of DDI at the protein level. Also, if the metabolic half-life of the drug is too long, then the CYP450 system again becomes the main elimination pathway, thus defeating the original purpose of the design. In order to avoid high peak concentrations and rapidly declining blood levels when administered, such a drug should also be administered using a delivery system that produces constant and controllable blood levels over time.

In various embodiments, the primary metabolites of the inventive compounds, regardless of the electrophysiological properties of the parent drug, has, or have, negligible inhibitory activity at the $IK_R$ (HERG) channel at normal therapeutic concentrations of the drug in plasma. In other words, the concentration of the metabolite can be at least five times higher than the normal therapeutic concentration of the parent compound before activity at the $IK_R$ channel is observed. Preferably, the concentration of the metabolite is at least ten times higher than the normal therapeutic concentration of the parent compound before activity at the $IK_R$ channel is observed.

Compounds according to the invention are, primarily, metabolized by endogenous hydrolytic enzymes via hydrolysable bonds engineered into their structures. The primary metabolites resulting from this metabolic pathway are water soluble and do not have, or show a reduced incidence of, DDI when administered with other medications (drugs). Non-limiting examples of hydrolysable bonds that can be incorporated into compounds according to the invention include amide, ester, carbonate, phosphate, sulfate, urea, urethane, glycoside, or other bonds that can be cleaved by hydrolases.

Additional modifications of the compounds disclosed herein can readily be made by those skilled in the art. Thus, analogs and salts of the exemplified compounds are within the scope of the subject invention. With a knowledge of the compounds of the subject invention skilled chemists can use known procedures to synthesize these compounds from available substrates. As used in this application, the term "analogs" refers to compounds which are substantially the same as another compound but which may have been modified by, for example, adding additional side groups. The term "analogs" as used in this application also may refer to compounds which are substantially the same as another compound but which have atomic or molecular substitutions at certain locations in the compound.

Analogs of the exemplified compounds can be readily prepared using commonly known, standard reactions. These standard reactions include, but are not limited to, hydrogenation, methylation, acetylation, and acidification reactions. For example, new salts within the scope of the invention can be made by adding mineral acids, e.g., HCl $H_2SO_4$, etc., or strong organic acids, e.g., formic, oxalic, etc., in appropriate amounts to form the acid addition salt of the parent compound or its derivative. Also, synthesis type reactions may be used pursuant to known procedures to add or modify various groups in the exemplified compounds to produce other compounds within the scope of the invention.

In a preferred embodiment, the subject invention provides compounds having Formula I:

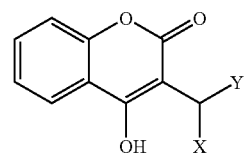

Formula I

Wherein:

X is independently in each occurrence hydrogen, alkyl, cycloalkyl, halogen, heterocyclyl, hydroxy, alkoxy, $R_2$, heteroaryl or aryl optionally substituted with $COOR_1$, or other group, including, for example, halogens.

$R_1$ is independently in each occurrence hydrogen, alkyl or alkylaryl, all optionally substituted with lower alkyl, hydroxy, halogen, or alkoxy.

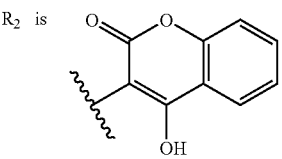

Y is independently in each occurrence $(CHR_3)_n COOR_4$ or aryl optionally substituted with $COOR_5$, wherein n=1 to 3.

$R_3$ is independently in each occurrence hydrogen, alkyl or alkylaryl, aryl all optionally substituted with lower alkyl, hydroxy, halogen, or alkoxy.

$R_4$ is independently in each occurrence hydrogen, alkyl or alkylaryl, aryl all optionally substituted with lower alkyl, hydroxy, halogen, or alkoxy.

$R_5$ is independently in each occurrence hydrogen, alkyl or alkylaryl, aryl all optionally substituted with lower alkyl, hydroxy, halogen, or alkoxy.

X and Y taken together can form butyrolactone when X is OH and Y is O-benzoic acid.

Reference herein to "lower alkyl" refers to $C_{1-8}$ alkyl. As used herein, "aryl" refers to any aromatic group. As set forth herein, the aryl group may be substituted or unsubstituted. Possible substituents include, but are not limited to, lower alkyl, hydroxyl, halogen, and alkoxy.

Specifically exemplified herein are the following compounds:

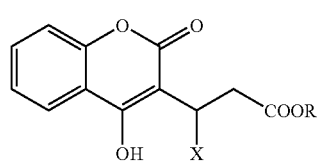

Formula II 3-(4-Hydroxy-2-oxo-2H-chromen-3-yl)-3-phenyl-propionic acid
3-(4-Hydroxy-2-oxo-2H-chromen-3-yl)-3-phenyl-propionic acid methyl ester
3-(4-Hydroxy-2-oxo-2H-chromen-3-yl)-3-phenyl-propionic acid ethyl ester
3-(4-Hydroxy-2-oxo-2H-chromen-3-yl)-3-phenyl-propionic acid n-propyl ester
3-(4-Hydroxy-2-oxo-2H-chromen-3-yl)-3-phenyl-propionic acid n-butyl ester
3-(4-Hydroxy-2-oxo-2H-chromen-3-yl)-3-phenyl-propionic acid 2-butyl ester
3-(4-Hydroxy-2-oxo-2H-chromen-3-yl)-3-phenyl-propionic acid isopropyl ester
3-Cyclohexyl-3-(4-hydroxy-2-oxo-2H-chromen-3-yl)-propionic acid
3-Cyclohexyl-3-(4-hydroxy-2-oxo-2H-chromen-3-yl)-propionic acid methyl ester
3-Cyclohexyl-3-(4-hydroxy-2-oxo-2H-chromen-3-yl)-propionic acid ethyl ester
3-Cyclohexyl-3-(4-hydroxy-2-oxo-2H-chromen-3-yl)-propionic acid n-propyl ester
3-Cyclopentyl-3-(4-hydroxy-2-oxo-2H-chromen-3-yl)-propionic acid
3-Cyclopentyl-3-(4-hydroxy-2-oxo-2H-chromen-3-yl)-propionic acid methyl ester
3-Cyclopentyl-3-(4-hydroxy-2-oxo-2H-chromen-3-yl)-propionic acid ethyl ester
3-Cyclopentyl-3-(4-hydroxy-2-oxo-2H-chromen-3-yl)-propionic acid n-propyl ester
3-Propyl-3-(4-hydroxy-2-oxo-2H-chromen-3-yl)-propionic acid
3-Propyl-3-(4-hydroxy-2-oxo-2H-chromen-3-yl)-propionic acid methyl ester
3-Propyl-3-(4-hydroxy-2-oxo-2H-chromen-3-yl)-propionic acid ethyl ester
3-Propyl-3-(4-hydroxy-2-oxo-2H-chromen-3-yl)-propionic acid n-propyl ester

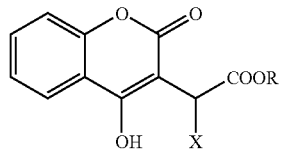

Formula III (4-Hydroxy-2-oxo-2H-chromen-3-yl)-phenyl-acetic acid
(4-Hydroxy-2-oxo-2H-chromen-3-yl)-phenyl-acetic acid methyl ester
(4-Hydroxy-2-oxo-2H-chromen-3-yl)-phenyl-acetic acid ethyl ester
(4-Hydroxy-2-oxo-2H-chromen-3-yl)-phenyl-acetic acid n-propyl ester
(4-Hydroxy-2-oxo-2H-chromen-3-yl)-phenyl-acetic acid 2-propyl ester
(4-Hydroxy-2-oxo-2H-chromen-3-yl)-phenyl-acetic acid n-butyl ester
2-(4-Hydroxy-2-oxo-2H-chromen-3-yl)-butyric acid
2-(4-Hydroxy-2-oxo-2H-chromen-3-yl)-butyric acid methyl ester
2-(4-Hydroxy-2-oxo-2H-chromen-3-yl)-butyric acid ethyl ester
2-(4-Hydroxy-2-oxo-2H-chromen-3-yl)-butyric acid n-propyl ester
2-(4-Hydroxy-2-oxo-2H-chromen-3-yl)-butyric acid isopropyl ester
2-(4-Hydroxy-2-oxo-2H-chromen-3-yl)-butyric acid n-butyl ester

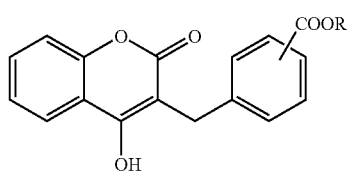

Formula IV 4-(4-Hydroxy-2-oxo-2H-chromen-3-ylmethyl)-benzoic acid
4-(4-Hydroxy-2-oxo-2H-chromen-3-ylmethyl)-benzoic acid methyl ester
4-(4-Hydroxy-2-oxo-2H-chromen-3-ylmethyl)-benzoic acid ethyl ester
4-(4-Hydroxy-2-oxo-2H-chromen-3-ylmethyl)-benzoic acid n-propyl ester
4-(4-Hydroxy-2-oxo-2H-chromen-3-ylmethyl)-benzoic acid n-butyl ester
2-(4-Hydroxy-2-oxo-2H-chromen-3-ylmethyl)-benzoic acid
2-(4-Hydroxy-2-oxo-2H-chromen-3-ylmethyl)-benzoic acid methyl ester
2-(4-Hydroxy-2-oxo-2H-chromen-3-ylmethyl)-benzoic acid ethyl ester
2-(4-Hydroxy-2-oxo-2H-chromen-3-ylmethyl)-benzoic acid n-propyl ester
2-(4-Hydroxy-2-oxo-2H-chromen-3-ylmethyl)-benzoic acid n-butyl ester
3-(4-Hydroxy-2-oxo-2H-chromen-3-ylmethyl)-benzoic acid
3-(4-Hydroxy-2-oxo-2H-chromen-3-ylmethyl)-benzoic acid methyl ester
3-(4-Hydroxy-2-oxo-2H-chromen-3-ylmethyl)-benzoic acid ethyl ester
3-(4-Hydroxy-2-oxo-2H-chromen-3-ylmethyl)-benzoic acid n-propyl ester
3-(4-Hydroxy-2-oxo-2H-chromen-3-ylmethyl)-benzoic acid n-butyl ester

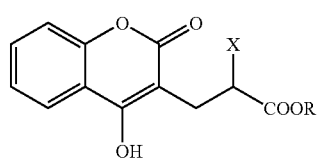

Formula V

2-Benzyl-3-(4-hydroxy-2-oxo-2H-chromen-3-yl)-propionic acid
2-Benzyl-3-(4-hydroxy-2-oxo-2H-chromen-3-yl)-propionic acid methyl ester
2-Benzyl-3-(4-hydroxy-2-oxo-2H-chromen-3-yl)-propionic acid ethyl ester
2-Benzyl-3-(4-hydroxy-2-oxo-2H-chromen-3-yl)-propionic acid n-propyl ester
2-Benzyl-3-(4-hydroxy-2-oxo-2H-chromen-3-yl)-propionic acid n-butyl ester
2-(4-Hydroxy-2-oxo-2H-chromen-3-ylmethyl)-butyric acid
2-(4-Hydroxy-2-oxo-2H-chromen-3-ylmethyl)-butyric acid methyl ester
2-(4-Hydroxy-2-oxo-2H-chromen-3-ylmethyl)-butyric acid ethyl ester 2-(4-Hydroxy-2-oxo-2H-chromen-3-ylmethyl)-butyric acid n-propyl ester 2-(4-Hydroxy-2-oxo-2H-chromen-3-ylmethyl)-butyric acid n-butyl ester

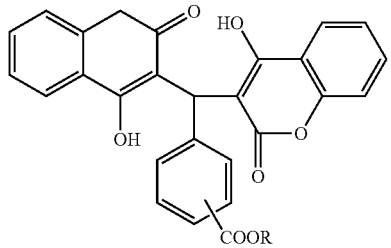

Formula VI

4-[(4-Hydroxy-2-oxo-2H-chromen-3-yl)-(4-hydroxy-1-oxo-1H-isochromen-3-yl)-methyl]-benzoic acid 4-[(4-Hydroxy-2-oxo-2H-chromen-3-yl)-(4-hydroxy-1-oxo-1H-isochromen-3-yl)-methyl]-benzoic acid methyl ester 4-[(4-Hydroxy-2-oxo-2H-chromen-3-yl)-(4-hydroxy-1-oxo-1H-isochromen-3-yl)-methyl]-benzoic acid ethyl ester 4-[(4-Hydroxy-2-oxo-2H-chromen-3-yl)-(4-hydroxy-1-oxo-1H-isochromen-3-yl)-methyl]-benzoic acid n-propyl ester 4-[(4-Hydroxy-2-oxo-2H-chromen-3-yl)-(4-hydroxy-1-oxo-1H-isochromen-3-yl)-methyl]-benzoic acid n-butyl ester 3-[(4-Hydroxy-2-oxo-2H-chromen-3-yl)-(4-hydroxy-1-oxo-1H-isochromen-3-yl)-methyl]-benzoic acid 3-[(4-Hydroxy-2-oxo-2H-chromen-3-yl)-(4-hydroxy-1-oxo-1H-isochromen-3-yl)-methyl]-benzoic acid methyl ester 3-[(4-Hydroxy-2-oxo-2H-chromen-3-yl)-(4-hydroxy-1-oxo-1H-isochromen-3-yl)-methyl]-benzoic acid ethyl ester 3-[(4-Hydroxy-2-oxo-2H-chromen-3-yl)-(4-hydroxy-1-oxo-1H-isochromen-3-yl)-methyl]-benzoic acid n-propyl ester 3-[(4-Hydroxy-2-oxo-2H-chromen-3-yl)-(4-hydroxy-1-oxo-1H-isochromen-3-yl)-methyl]-benzoic acid n-butyl ester 2-[(4-Hydroxy-2-oxo-2H-chromen-3-yl)-(4-hydroxy-1-oxo-1H-isochromen-3-yl)-methyl]-benzoic acid 2-[(4-Hydroxy-2-oxo-2H-chromen-3-yl)-(4-hydroxy-1-oxo-1H-isochromen-3-yl)-methyl]-benzoic acid methyl ester 2-[(4-Hydroxy-2-oxo-2H-chromen-3-yl)-(4-hydroxy-1-oxo-1H-isochromen-3-yl)-methyl]-benzoic acid ethyl ester 2-[(4-Hydroxy-2-oxo-2H-chromen-3-yl)-(4-hydroxy-1-oxo-1H-isochromen-3-yl)-methyl]-benzoic acid n-propyl ester 2-[(4-Hydroxy-2-oxo-2H-chromen-3-yl)-(4-hydroxy-1-oxo-1H-isochromen-3-yl)-methyl]-benzoic acid n-butyl ester

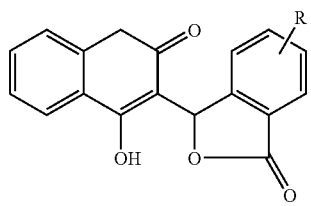

Formula VII 3-(1-Hydroxy-3-oxo-3,4-dihydro-naphthalen-2-yl)-3H-isobenzofuran-1-one In Formulae II–VII "R" is defined consistent with the exemplified compounds, as well as including the various groups included in the definition of "X" in Formula I.

Further specific embodiments of the subject invention include the following compounds:

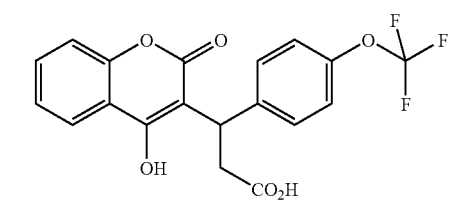

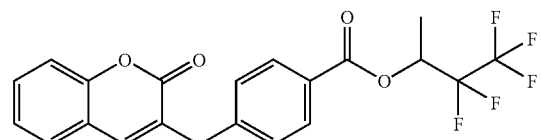

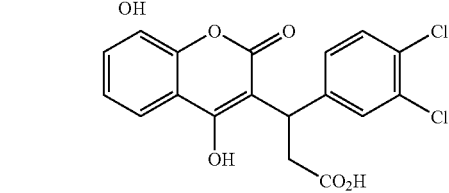

Advantageously, these halogenated compounds are less favorable substrates for cytochrome P450 than their unhalogenated analogs. They are therefore more likely to be metabolized by esterases, which is desirable for eliminating drug-drug interactions according to the subject invention.

The subject invention also provides processes for the manufacturing of novel coumarin derivatives. Examples of synthetic schemes are as follows:

Scheme 1 provides an exemplary synthesis of C-3 substituted 4-hydroxycoumarins. Appropriately substituted bromoacetate and 4-hydroxycoumarin in the presence of a base give mixture of O and C-3 alkylated 4-hydroxy coumarins, which are readily separable.

Scheme 2 provides an alternative synthesis of C-3 substituted 4-hydroxycoumarins when $R_1$ is aryl groups. 4-hydroxycoumarin and an aromatic aldehyde can be heated in a mixture of triethylamine and formic acid (2:5 molar ratio) to give 3-benzyl-4-hydroxycoumarin, which was in turn treated with 2.2 eq. of BuLi and quenched with carbon dioxide to give coumarin substituted phenyl-acetic acid. Corresponding esters can be obtained by treating the acid with various alcohols in the presence of concentrated sulfuric acid.

Scheme 3 illustrates the synthesis of chromen-3-yl-propionic acid. 4-hyroxycoumarin, an appropriate aldehyde and meldrum's acid can be heated in EtOH in the presence ammonium acetate to give substituted propionate, which can then be treated with 2 eq. of LDA and an alkylating agent to provide the chromen-3-yl-propionionates.

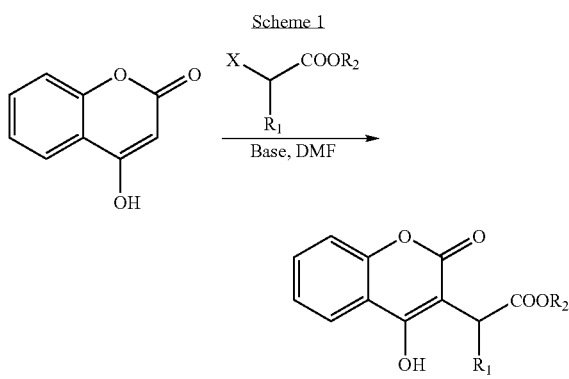

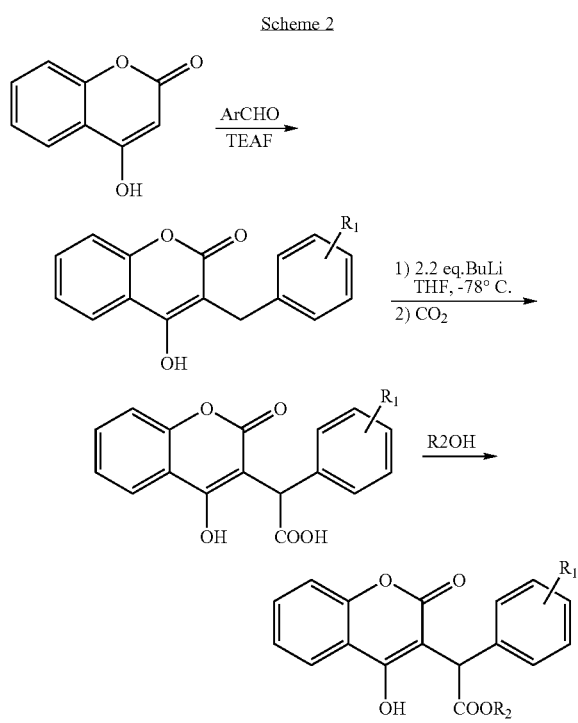

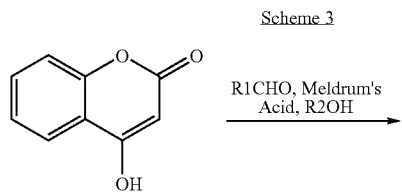

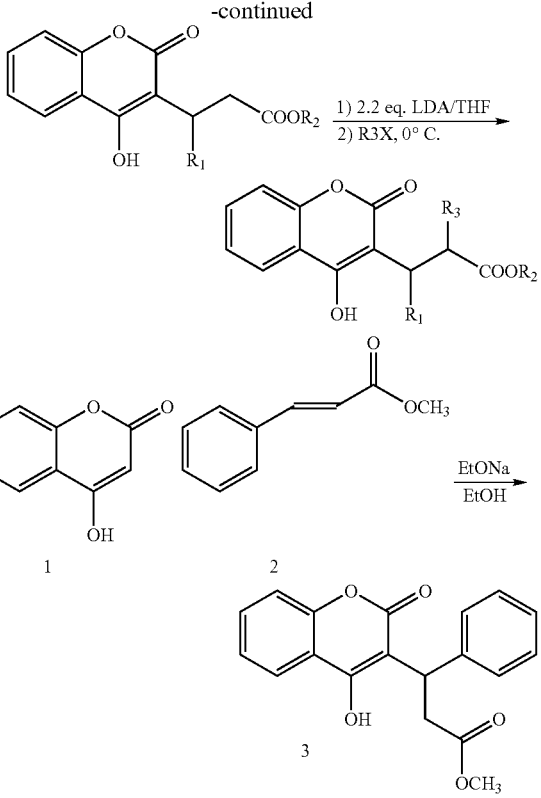

Exemplary reaction schemes for the production of derivatives of 7-hydroxycoumarin which have anti-coagulant properties are provided below. The synthesis of 4-Hydroxy-3-(3-methoxy-3-oxo-1-phenylpropyl)-2H-1-benzopyran-2-one 3 is performed by Michael condensation of 4-Hydroxycoumarin 1 and methyl trans-cinnamate 2 in absolute ethanol in the presence of sodium ethoxide at reflux temperature for 16 hours.

Knoevenagel reaction between 4-Hydroxycoumarin 1 and benzaldehyde 4 in the presence of piperidinium benzoate gives the benzal adduct 5. Michael addition between 5 and ethoxycarbonylmethyldimethylsulfide in toluene in the presence of DBU as a base gives the cyclopropane derivative 6. Michael addition between 5 and diethyl malonate in absolute ethanol with sodium ethoxide gives 7.

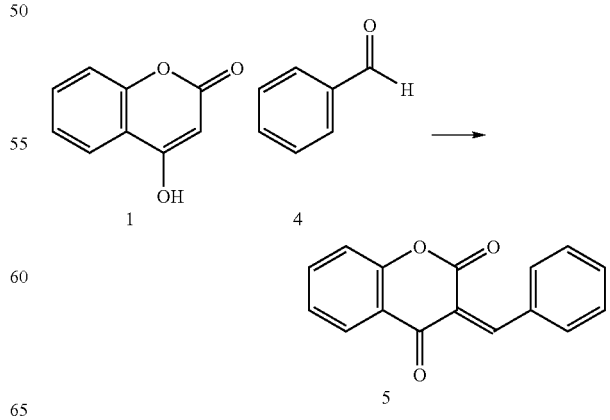

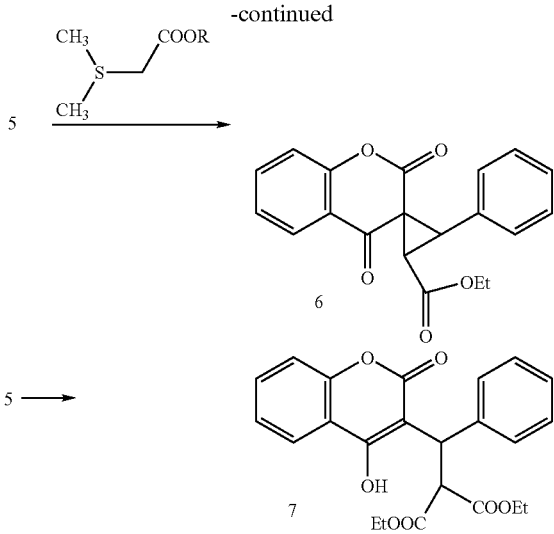

The subject invention further pertains to enantiomerically isolated compounds, and compositions comprising the compounds, for the treatment of coagulation disorders. The isolated enantiomeric forms of the compounds of the invention are substantially free from one another (i.e., in enantiomeric excess). In other words, the "R" forms of the compounds are substantially free from the "S" forms of the compounds and are, thus, in enantiomeric excess of the "S" forms. Conversely, "S" forms of the compounds are substantially free of "R" forms of the compounds and are, thus, in enantiomeric excess of the "R" forms. In one embodiment of the invention, the isolated enantiomeric compounds are at least about in 80% enantiomeric excess. In a preferred embodiment, the compounds are in at least about 90% enantiomeric excess. In a more preferred embodiment, the compounds are in at least about 95% enantiomeric excess. In an even more preferred embodiment, the compounds are in at least about 97.5% enantiomeric excess. In a most preferred embodiment, the compounds are in at least 99% enantiomeric excess.

The subject invention also provides methods for treating coagulation disorders comprising the administration of a therapeutically effective amount of the esterified warfarin analogs of this invention to an individual in need of treatment. The warfarin analogs of this invention have applicability in both veterinary and human clinical contexts. Further, the compounds of this invention have therapeutic properties similar to those of the unmodified parent compound (COUMADINE). Accordingly, dosage rates and routes of administration of the disclosed compounds are similar to those already used in the art and known to the skilled artisan (see, for example, *Physicians' Desk Reference*, 54th Ed., Medical Economics Company, Montvale, N.J., 2000 or U.S. Pat. No. 5,856,525 hereby incorporated by reference in its entirety).

The compounds of the subject invention can be formulated according to known methods for preparing pharmaceutically useful compositions. Formulations are described in detail in a number of sources which are well known and readily available to those skilled in the art. For example, *Remington's Pharmaceutical Science* by E. W. Martin describes formulations which can be used in connection with the subject invention. In general, the compositions of the subject invention will be formulated such that an effective amount of the bioactive compound(s) is combined with a suitable carrier in order to facilitate effective administration of the composition.

In accordance with the invention, pharmaceutical compositions comprising, as an active ingredient, an effective amount of one or more of the compounds and one or more non-toxic, pharmaceutically acceptable carrier or diluent. Examples of such carriers for use in the invention include ethanol, dimethyl sulfoxide, glycerol, silica, alumina, starch, and equivalent carriers and diluents.

Further, acceptable carriers can be either solid or liquid. Solid form preparations include powders, tablets, pills, capsules, cachets, suppositories and dispersible granules. A solid carrier can be one or more substances which may act as diluents, flavoring agents solubilizers, lubricants, suspending agents, binders, preservatives, tablet disintegrating agents or an encapsulating material.

The disclosed pharmaceutical compositions may be subdivided into unit doses containing appropriate quantities of the active component. The unit dosage form can be a packaged preparation, such as packeted tablets, capsules, and powders in paper or plastic containers or in vials or ampoules. Also, the unit dosage can be a liquid based preparation or formulated to be incorporated into solid food products, chewing gum, or lozenge.

The term "individual(s)" is defined as a single mammal to which is administered a compound of the present invention. The mammal may be a rodent, for example a mouse or rat, pig, horse, rabbit, goat, pig, cow, cat, dog, or human. In a preferred embodiment, the individual is a human.

Following are examples which illustrate procedures for practicing the invention. These examples should not be construed as limiting. All percentages are by weight and all solvent mixture proportions are by volume unless otherwise noted.

EXAMPLE 1

Preparation of 2-(4-Hydroxy-2-oxo-2H-chromen-3-yl)-butyric acid ethyl ester

To a solution of 4-hydroxy-chromen-2-one (2.0 g) and ethyl 2-bromobutyrate (2 mL) in DMF was added anhydrous potassium carbonate (8.5 g). The resulting reaction mixture was stirred at room temperature for 72 hours, then diluted with water and extracted with EtOAc. The organic layer was washed with saturated aqueous sodium bicarbonate, dried over MgSO4 and conc. in vacuo to provide colorless oil, which was purified by column chromatography to give 2-(4-Hydroxy-2-oxo-2H-chromen-3-yl) -butyric acid ethyl ester as a white solid, MS: 275[M–H].

EXAMPLE 2

Preparation of 2-Benzyl-3-(4-hydroxy-2-oxo-2H-chromen-3-yl)-propionic acid ethyl ester A solution of 4-hydroxy-chromen-2-one (2.0 g), aqueous formaldehyde (37%, 0.37 g), Meldrum's acid (1.77 g) and ammonium acetate (0.95 g) in ethanol (75 mL) was heated to reflux for 6 hours, then cooled to room temperature. The reaction mixture was conc. in vacuo to give the crude as yellow oil, which was purified by column chromatography to provide 3-(4-Hydroxy-2-oxo-2H-chromen-3-yl)-propionic acid ethyl ester as colorless oil (1.2 g).

To a solution of 3-(4-Hydroxy-2-oxo-2H-chromen-3-yl)-propionic acid ethyl ester in THF at −78° C. was added LDA (1.5M, 3.05 mL) dropwise. A yellow precipitate was formed during the addition. The reaction was stirred at −78° C. for 15 min and allowed to warmed to 0° C. and stirred for 30 min, after which BnBr (0.24 mL in THF) was added dropwise. The reaction was warmed to room temperature, stirred for 12 hours, cooled to 0° C. and quenched with saturated ammonium chloride and extracted with EtOAc. The organic layer was washed with brine, dried over MgSO4 and conc. in vacuo to a crude colorless oil, which was purified by column chromatography to provide 2-Benzyl-3-(4-hydroxy-2-oxo-2H-chromen-3-yl)-propionic acid ethyl ester as a colorless oil (250 mg). MS: 351[M−H].

EXAMPLE 3

Preparation of 2-Benzyl-3-(4-hydroxy-2-oxo-2H-chromen-3-yl)-propionic acid

2-Benzyl-3-(4-hydroxy-2-oxo-2H-chromen-3-yl)-propionic acid ethyl ester (160 mg) in EtOH (1 mL) was added 1N NaOH (1.36 mL). The resulting mixture was heated to 50° C. and stirred for 2 hours, cooled to room temperature, acidified with Conc. HCl/ice and extracted with ether. The organic layer was dried over MgSO4 and conc. in vacuo to give 2-Benzyl-3-(4-hydroxy-2-oxo-2H-chromen-3-yl)-propionic acid as a pale yellow solid (120 mg). MS: 323[M−H].

EXAMPLE 4

Preparation of (4-Hydroxy-2-oxo-2H-chromen-3-yl)-phenyl-acetic acid ethyl ester

Triethylammonium formate (TEAF) was prepared by adding TEA (20.0 mL) to formic acid (16.5 mL) with ice cooling. To TEAF was added benzaldehyde (3.78 mL) and 4-hydroxy-chromen-2-one (6.0 g) and the resulting mixture was heated to 130–140° C. for 3 hours, cooled to room temperature, diluted with water, and extracted with EtOAc. The organic layer was washed with brine, dried over MgSO4 and conc. in vacuo to give a light yellow solid. The crude solid was recrystallized from EtOH to give 3-Benzyl-4-hydroxy-chromen-2-one as a white solid (1.95 g).

To a solution of 3-Benzyl-4-hydroxy-chromen-2-one (2.0 g) in THF at −78° C. was added BuLi (1.6M, 11.4 mL) dropwise during which a yellow precipitate was formed. The reaction was stirred at −78° C. for 30 min and carbon dioxide gas was bubbled through for 10 min, warmed to 0° C. and quenched with saturated ammonium chloride, extracted with EtOAc (3×50 mL). The aqueous phase was acidified with conc. HCl and extracted with EtOAc. The organic layer was dried over MgSO4 and conc. in vacuo to provide a colorless oil, which crystallize up standing to give (4-Hydroxy-2-oxo-2H-chromen-3-yl)-phenyl-acetic acid as a white solid (920 mg). MS: 295[M−H].

A solution of (4-Hydroxy-2-oxo-2H-chromen-3-yl)-phenyl-acetic acid in EtOH with a catalytic amount of conc. sulfuric acid was heated to reflux for 5 hours, cooled to room temperature, diluted with water and extracted with EtOAc. The organic layer was dried over MgSO4 and conc. in vacuo to give (4-Hydroxy-2-oxo-2H-chromen-3-yl)-phenyl-acetic acid ethyl ester as colorless oil, which crystallize upon standing (910 mg). MS: 323[M−H].

EXAMPLE 5

Preparation of 4-Hydroxy-3-(3-oxo-1,3-dihydro-isobenzofuran-1-yl)-chromen-2-one

A solution of 4-hydroxy-chromen-2-one (650 mg) and 2-carboxybenzyladehyde (300 mg) in EtOH was heated to reflux for 4 hours, cooled to room temperature then concentrated in vacuo to give a crude oil, which was diluted with water. The precipitated 4-hydroxy-chromen-2-one was collected by filtration (490 mg). A second crop of solid was collected from the mother liquor and triturated with hot EtOAc and filtered to provide 4-Hydroxy-3-(3-oxo-1,3-dihydro-isobenzofuran-1-yl)-chromen-2-one as white solid. MS: 293 [M−H].

EXAMPLE 6

Preparation of 2-(4-Hydroxy-2-oxo-2H-chromen-3-ylmethyl)-benzoic acid methyl ester To a solution 4-Hydroxy-3-(3-oxo-1,3-dihydro-isobenzofuran-1-yl)-chromen-2-one (60 mg) in ethanol was added 10% Pd/C (10 mg) then stirred under a hydrogen balloon for 12 hours. The reaction mixture was filtered through a pad of celite and the filtrate was concentrated in vacuo to give 2-(4-Hydroxy-2-oxo-2H-chromen-3-ylmethyl)-benzoic acid as white solid (50 mg). MS: 295[M−H].

A solution of 2-(4-Hydroxy-2-oxo-2H-chromen-3-ylmethyl)-benzoic acid in MeOH with a catalytic amount of conc. sulfuric acid was heated to reflux for 5 hours, cooled to room temperature, diluted with water and extracted with EtOAc. The organic layer was dried over MgSO4 and conc. in vacuo to give 2-(4-Hydroxy-2-oxo-2H-chromen-3-ylmethyl)-benzoic acid methyl ester as white solid. MS: 309 [M−H].

EXAMPLE 7

Mice In Vivo, Bleeding Time

Test substance was administered orally (30, 10 and 3 mg/kg) to a group of 3 ICR derived male or female mice weighing 22±2 grams, respectively, at 18, 24 and 30 hours before standardized transection of the tip (0.5 mm) of each tail. The mice, in holders, were immediately suspended vertically with the distal 2 cm of each tail immersed in a test tube containing saline at 37° C. The time required for beginning a 15 second period of bleeding cessation is then determined; a maximum cut-off time of 180 seconds is used. Prolongation of bleeding time by 50 percent or more (≧50%) relative to a control group of animals was considered significant.

EXAMPLE 8

Selected Compounds of the Subject Invention

The subject invention is demonstrated in the production of warfarin analogs which have been designed to be metabolized by esterase enzymes. Exemplary compounds include structures of the formula:

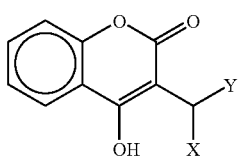

X = H or CH$_2$ COOH

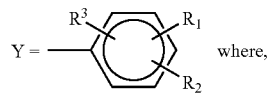 where,

R$_1$, R$_2$ and R$_3$ can occupy any position on the ring; and are, independently, H, Cl, F, I, lower alkoxy or substituted lower alkoxy, CN, NO$_2$, NH$_2$, or —COOR$_4$ where R$_4$ is lower alkyl or substituted alkyl.

Or, either 2 of R$_1$, R$_2$, and R$_3$ are independently methylene, methyne, O, S, NH and together are part of a 5–7-membered cyclic structure, wherein the cyclic structure can be substituted as defined above with respect to Y.

Preferred salts are sodium salts.

Specific compounds are as follows:

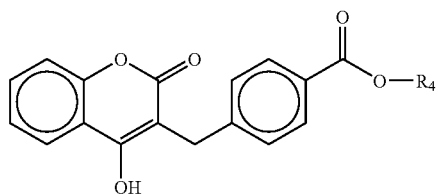

where R$_4$ is fluorinated or chlorinated lower alkyl having 1–10 carbon atoms (preferred is 1–6 carbon atoms).

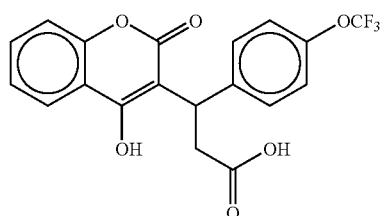

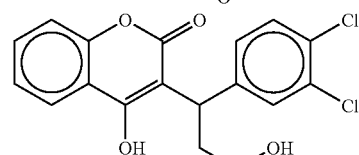

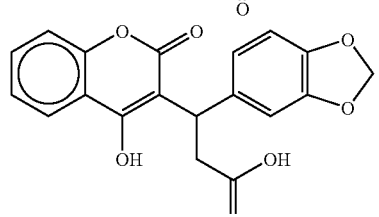

Additional compounds are:

wherein

R$_1$ is selected from the group consisting of —CH$_2$—COO—R$_5$, —CH(COOR$_5$)$_2$;

R$_2$ is H;

R$_3$ is selected from the group consisting of C$_{1-4}$ alkyl, phenyl, and benzyl; and, R$_4$ is H or a halogen; and, R$_5$ is selected from the group consisting of C$_{1-4}$ alkyl, phenyl, and benzyl groups.

Other embodiments of this invention contemplate compounds of the formulae:

wherein R is selected from the group consisting of C$_{1-4}$ alkyl, phenyl, and benzyl groups and R$_4$ is defined as above, H or a halogen.

Further specific embodiments include the following:

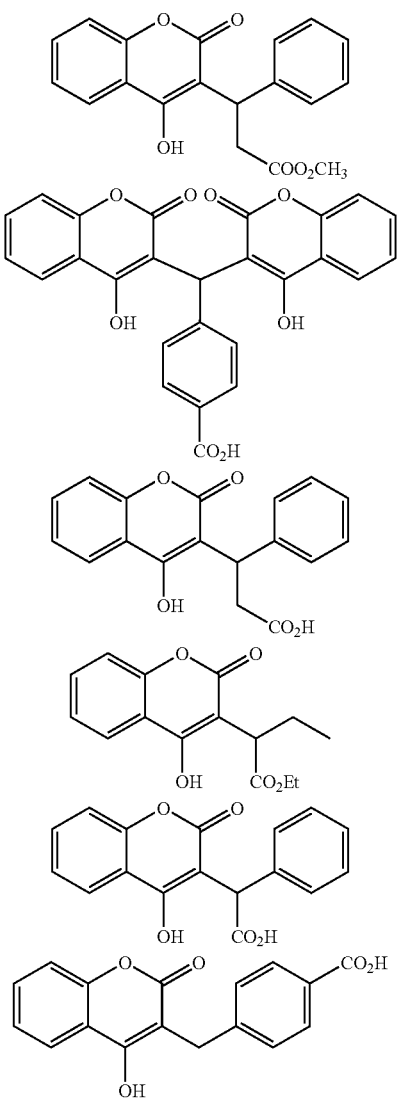

EXAMPLE 9

Halogenated Compounds

In certain embodiments, the subject invention provides compounds having Formula I:

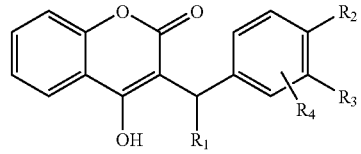

Formula I wherein:
$R_1$ is H or $CH_2COOH$;
$R_2$, $R_3$, and $R_4$ are independently H, Cl, $OCF_3$, or $COOR_5$, in which at least one of $R_2$, $R_3$, and $R_4$ is $COOR_5$, where $R_5$ is a halogenated alkyl, cycloalkyl, heteroalkyl, heterocycloalkyl, aryl, or heteroaryl group, comprising at least 1 halogen atom into its structure, preferably fluorine or chlorine, and which can be optionally substituted with other halogens atoms, OH, O-alkyl, or O-fluorinated alkyl.

Alternatively, $R_2$ and $R_3$ together can form an aromatic structure to give Formula II:

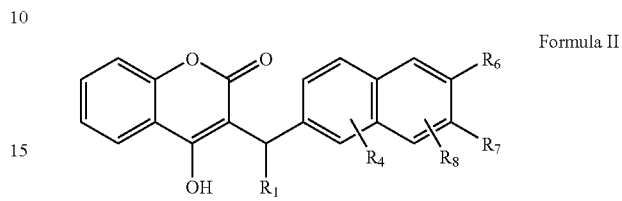

Formula II wherein:
$R_1$ is H or $CH_2COOH$;
$R_4$ is H, Cl, $OCF_3$; and
$R_6$, $R_7$, and $R_8$ are independently H, Cl, $OCF_3$, or $COOR_9$, in which at least one of $R_6$, $R_7$, and $R_8$ is $COOR_9$, where $R_9$ is a halogenated alkyl, cycloalkyl, heteroalkyl, heterocycloalkyl, aryl, or heteroaryl group, comprising at least 1 halogen atom into its structure, preferably fluorine or chlorine, and which can be optionally substituted with other halogens atoms, OH, O-alkyl, or O-fluorinated alkyl.

The subject invention also provides compounds of Formula I and Formula II wherein $R_5$ and $R_9$ are H. Compounds where $R_5$ and $R_9$ are H are the primary metabolites when compounds of Formula I and II are administered to a mammal, including human. They are essentially devoid of activity at the VKER enzyme, but they are useful for monitoring drug levels in patients.

Specific embodiments of the present invention include the following compounds:

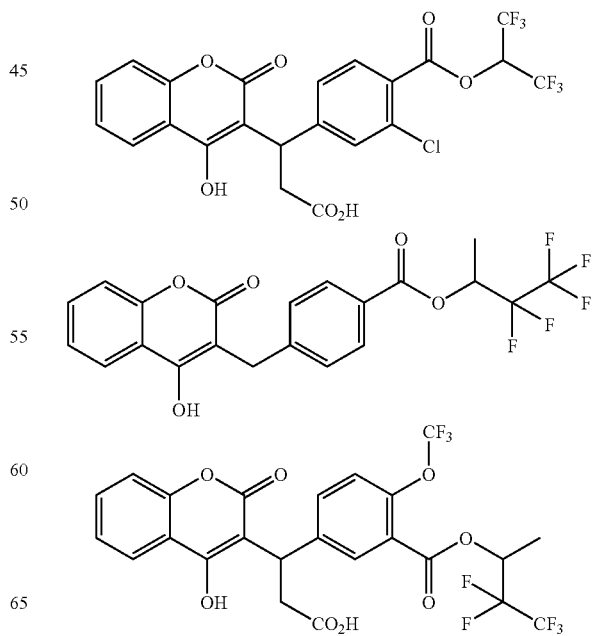

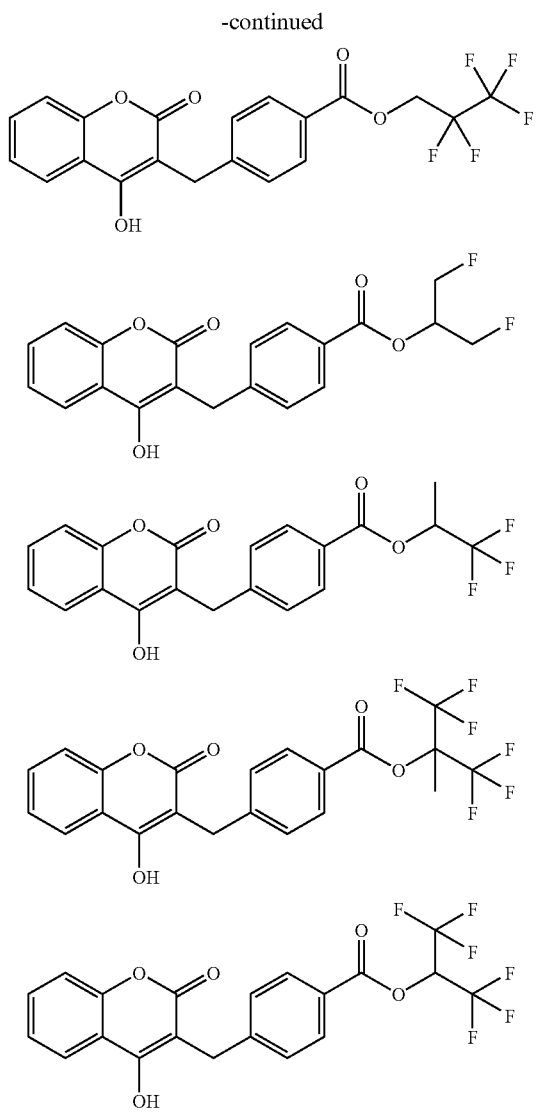

Advantageously, these halogenated compounds are less favorable substrates for cytochrome CYP450 than their unhalogenated analogs. They are therefore more likely to be metabolized by esterases, which is desirable for eliminating drug-drug interactions according to the subject invention.

The subject invention also provides processes for the manufacturing of the novel compounds. The synthesis of these compounds can be achieved as shown in schemes 1 and 2.

Scheme 1:

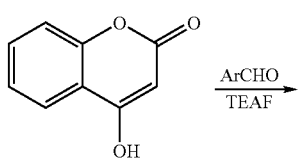

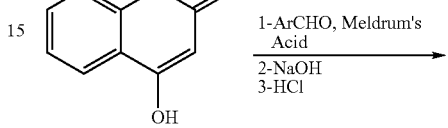

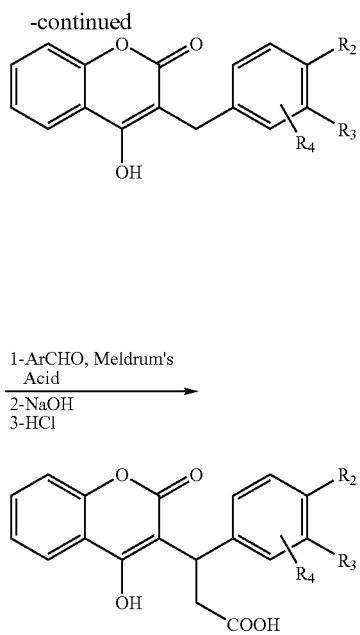

Scheme 2:

In scheme 1,4-hydroxycoumarin and a substituted aromatic aldehyde can be heated in a mixture of triethylamine and formic acid (2:5 molar ratio) to give the correspondingly substituted 3-benzyl-4-hydroxycoumarin wherein $R_1$ is hydrogen. Scheme 2 describes the synthetic pathway where $R_1$ is $CH_2COOH$. In scheme 2,4-hydroxycoumarin, an appropriately substituted aromatic aldehyde, and meldrum's acid can be heated in ethanol in the presence of ammonium acetate to give the correspondingly substituted chromen-3-yl-propionate, which in turn can be hydrolyzed using a base such as NaOH followed by acidification in order to provide the chromen-3-yl-propionic acid where $R_2$, $R_3$, and $R_4$ are defined as above.

The subject invention further pertains to enantiomerically pure compounds, and compositions comprising the compounds, for the treatment of coagulation disorders. The isolated enantiomeric forms of the compounds of the invention are substantially free from one another (i.e., in enantiomeric excess). In other words, the "R" forms of the compounds are substantially free from the "S" forms of the compounds and are, thus, in enantiomeric excess of the "S" forms. Conversely, "S" forms of the compounds are substantially free of "R" forms of the compounds and are, thus, in enantiomeric excess of the "R" forms. In one embodiment of the invention, the isolated enantiomeric compounds are at least about in 80% enantiomeric excess. In a preferred embodiment, the compounds are in at least about 90% enantiomeric excess. In a more preferred embodiment, the compounds are in at least about 95% enantiomeric excess. In an even more preferred embodiment, the compounds are in at least about 97.5% enantiomeric excess. In a most preferred embodiment, the compounds are in at least 99% enantiomeric excess.

Modifications of the compounds disclosed herein can readily be made by those skilled in the art. Thus, analogs, derivatives, and salts of the exemplified compounds are within the scope of the subject invention. With a knowledge of the compounds of the subject invention, and their structures, skilled chemists can use known procedures to synthesize these compounds from available substrates.

All patents, patent applications, provisional applications, and publications referred to or cited herein are incorporated by reference in their entirety, including all figures and tables, to the extent they are not inconsistent with the explicit teachings of this specification. Any compounds specifically disclosed in Synthetic Communications Journal (1993) 25:631–640 are specifically excluded from the scope of the compounds of the subject invention.

It should be understood that the examples and embodiments described herein are for illustrative purposes only and that various modifications or changes in light thereof will be suggested to persons skilled in the art and are to be included within the spirit and purview of this application.

The invention claimed is:

1. A compound or pharmaceutically acceptable salt thereof, that is
- 3-(1-Hydroxy-3-oxo-3,4-dihydro-naphthalen-2-yl)-3H-isobenzofuran-1-one;
- 3-Cyclohexyl-3-(4-hydroxy-2-oxo-2H-chromen-3-yl)-propionic acid;
- 3-Cyclohexyl-3-(4-hydroxy-2-oxo-2H-chromen-3-yl)-propionic acid methyl ester;
- 3-Cyclohexyl-3-(4-hydroxy-2-oxo-2H-chromen-3-yl)-propionic acid ethyl ester;
- 3-Cyclohexyl-3-(4-hydroxy-2-oxo-2H-chromen-3-yl)-propionic acid n-propyl ester;
- 3-Cyclopentyl-3-(4-hydroxy-2-oxo-2H-chromen-3-yl)-propionic acid;
- 3-Cyclopentyl-3-(4-hydroxy-2-oxo-2H-chromen-3-yl)-propionic acid methyl ester;
- 3-Cyclopentyl-3-(4-hydroxy-2-oxo-2H-chromen-3-yl)-propionic acid ethyl ester;
- 3-Cyclopentyl-3-(4-hydroxy-2-oxo-2H-chromen-3-yl)-propionic acid n-propyl ester;
- 3-Propyl-3-(4-hydroxy-2-oxo-2H-chromen-3-yl)-propionic acid;
- 3-Propyl-3-(4-hydroxy-2-oxo-2H-chromen-3-yl)-propionic acid methyl ester;
- 3-Propyl-3-(4-hydroxy-2-oxo-2H-chromen-3-yl)-propionic acid ethyl ester;
- 3-Propyl-3-(4-hydroxy-2-oxo-2H-chromen-3-yl)-propionic acid n-propyl ester;
- (4-Hydroxy-2-oxo-2H-chromen-3-yl)-phenyl-acetic acid;
- (4-Hydroxy-2-oxo-2H-chromen-3-yl)-phenyl-acetic acid methyl ester;
- (4-Hydroxy-2-oxo-2H-chromen-3-yl)-phenyl-acetic acid ethyl ester;
- (4-Hydroxy-2-oxo-2H-chromen-3-yl)-phenyl-acetic acid n-propyl ester;
- (4-Hydroxy-2-oxo-2H-chromen-3-yl)-phenyl-acetic acid 2-propyl ester;
- (4-Hydroxy-2-oxo-2H-chromen-3-yl)-phenyl-acetic acid n-butyl ester;
- 2-(4-Hydroxy-2-oxo-2H-chromen-3-yl)-butyric acid;
- 2-(4-Hydroxy-2-oxo-2H-chromen-3-yl)-butyric acid methyl ester;
- 2-(4-Hydroxy-2-oxo-2H-chromen-3-yl) butyric acid ethyl ester;
- 2-(4-Hydroxy-2-oxo-2H-chromen-3-yl)-butyric acid n-propyl ester;
- 2-(4-Hydroxy-2-oxo-2H-chromen-3-yl)-butyric acid iso-propyl ester;
- 2-(4-Hydroxy-2-oxo-2H-chromen-3-yl)-butyric acid n-butyl ester;
- 4-(4-Hydroxy-2-oxo-2H-chromen-3-ylmethyl)-benzoic acid;
- 4-(4-Hydroxy-2-oxo-2H-chromen-3-ylmethyl)-benzoic acid methyl ester;
- 4-(4-Hydroxy-2-oxo-2H-chromen-3-ylmethyl)-benzoic acid ethyl ester;
- 4-(4-Hydroxy-2-oxo-2H-chromen-3-ylmethyl)-benzoic acid n-propyl ester;
- 4-(4-Hydroxy-2-oxo-2H-chromen-3-ylmethyl)-benzoic acid n-butyl ester;
- 2-(4-Hydroxy-2-oxo-2H-chromen-3-ylmethyl)-benzoic acid;
- 2-(4-Hydroxy-2-oxo-2H-chromen-3-ylmethyl)-benzoic acid methyl ester;
- 2-(4-Hydroxy-2-oxo-2H-chromen-3-ylmethyl)-benzoic acid ethyl ester;
- 2-(4-Hydroxy-2-oxo-2H-chromen-3-ylmethyl)-benzoic acid n-propyl ester;
- 2-(4-Hydroxy-2-oxo-2H-chromen-3-ylmethyl)-benzoic acid n-butyl ester;
- 3-(4-Hydroxy-2-oxo-2H-chromen-3-ylmethyl) benzoic acid;
- 3-(4-Hydroxy-2-oxo-2H-chromen-3-ylmethyl)-benzoic acid methyl ester;
- 3-(4-Hydroxy-2-oxo-2H-chromen3-ylmethyl)-benzoic acid ethyl ester;
- 3-(4-Hydroxy-2-oxo-2H-chromen-3-ylmethyl)-benzoic acid n-propyl ester;
- 3-(4-Hydroxy-2-oxo-2H-chromen-3-ylmethyl)-benzoic acid n-butyl ester;
- 2-Benzyl-3-(4-hydroxy-2-oxo-2H-chromen-3-yl)-propionic acid;
- 2-Benzyl-3-(4-hydroxy-2-oxo-2H-chromen-3-yl)-propionic acid methyl ester;
- 2-Benzyl-3-(4-hydroxy-2-oxo-2H-chromen-3-yl)-propionic acid ethyl ester;
- 2-Benzyl-3-(4-hydroxy-2-oxo-2H-chromen-3-yl)-propionic acid n-propyl ester;
- 2-Benzyl-3-(4-hydroxy-2-oxo-2H-chromen-3-yl)-propionic acid n-butyl ester;
- 2-(4-Hydroxy-2-oxo-2H-chromen-3-ylmethyl)-butyric acid;
- 2-(4-Hydroxy-2-oxo-2H-chromen-3-ylmethyl)-butyric acid methyl ester;
- 2-(4-Hydroxy-2-oxo-2H-chromen-3-ylmethyl)-butyric acid ethyl ester;
- 2-(4-Hydroxy-2-oxo-2H-chromen-3-ylmethyl)-butyric acid n-propyl ester;
- 2-(4-Hydroxy-2-oxo-2H-chromen-3-ylmethyl)-butyric acid n-butyl ester;
- 4-[(4-Hydroxy-2-oxo-2H-chromen-3-yl) (4-hydroxy-1-oxo-1H-isochromen-3-yl)-methyl]-benzoic acid methyl ester;
- 4-[(4-Hydroxy-2-oxo-2H-chromen-3-yl)-(4-hydroxy-1-oxo-1H-isochromen-3-yl)-methyl]-benzoic acid ethyl ester;
- 4-[(4-Hydroxy-2-oxo-2H-chromen-3-yl)-(4-hydroxy-1-oxo-1H-isochromen-3-yl)-methyl]-benzoic acid n-propyl ester;
- 4-[(4-Hydroxy-2-oxo-2H-chromen-3-yl)-(4-hydroxy-1-oxo-1H-isochromen-3-yl)-methyl]-benzoic acid n-butyl ester;
- 3-[(4-Hydroxy-2-oxo-2H-chromen-3-yl)-(4-hydroxy-1-oxo-1H-isochromen-3-yl)-methyl]benzoic acid;
- 3-[(4-Hydroxy-2-oxo-2H-chromen-3-yl)-(4-hydroxy-1-oxo-1H-isochromen-3-yl)-methyl]-benzoic acid methyl ester;

3-[(4-Hydroxy-2-oxo-2H-chromen-3-yl)-(4-hydroxy-1-oxo-1H -isochromen-3-yl)-methyl]-benzoic acid ethyl ester;
3-[(4-Hydroxy-2-oxo-2H-chromen-3-yl)-(4-hydroxy-1-oxo-1H -isochromen-3-yl)-methyl]-benzoic acid n-propyl ester;
3-[(4-Hydroxy-2-oxo-2H-chromen-3-yl)-(4-hydroxy-1-oxo-1H -isochromen-3-yl)-methyl]-benzoic acid n-butyl ester;
2-[(4-Hydroxy-2-oxo-2H-chromen-3-yl)-(4-hydroxy-1-oxo-1H -isochromen-3-yl)-methyl]-benzoic acid;
2-[(4-Hydroxy-2-oxo-2H-chromen-3-yl)-(4-hydroxy-1-oxo-1H -isochromen-3-yl)-methyl]-benzoic acid methyl ester;
2-[(4-Hydroxy-2-oxo-2H-chromen-3-yl)-(4-hydroxy-1-oxo-1H -isochromen-3-yl)-methyl]-benzoic acid ethyl ester;
2[(4Hydroxy-2-oxo-2H-chromen-3-yl)-(4-hydroxy-1-oxo-1H -isochromen-3-yl)-methyl]-benzoic acid n-propyl ester; or
2-[(4-Hydroxy-2-oxo-2H-chromen-3-yl)-(4-hydroxy-1-oxo-1H -isochromen-3-yl)-methyl]-benzoic acid n-butyl ester.

2. A compound or salt according to claim 1 that is
3-(1-Hydroxy-3-oxo-3,4-dihydro-naphthalen-2-yl) 3H -isobenzofuran-1-one.

3. A compound or salt according to claim 1 that is
3-Cyclohexyl-3-(4-hydroxy-2-oxo-2H-chromen-3-yl)-propionic acid;
3-Cyclohexyl-3-(4-hydroxy-2-oxo-2H-chromen-3-yl)-propionic acid methyl ester;
3-Cyclohexyl-3-(4-hydroxy-2-oxo-2H-chromen-3-yl)-propionic acid ethyl ester;
3-Cyclohexyl-3-(4-hydroxy-2-oxo-2H-chromen-3-yl)-propionic acid n-propyl ester; or
3-Cyclopentyl-3-(4-hydroxy-2-oxo-2H-chromen-3-yl)-propionic acid.

4. A compound or salt according to claim 1 that is
3-Cyclopentyl-3-(4-hydroxy-2-oxo-2H-chromen-3-yl)-propionic acid methyl ester;
3-Cyclopentyl-3-(4-hydroxy-2-oxo-2H-chromen-3-yl)-propionic acid ethyl ester;
3-Cyclopentyl-3-(4-hydroxy-2-oxo-2H-chromen-3-yl)-propionic acid n-propyl ester;
3-Propyl-3-(4-hydroxy-2-oxo-2H-chromen-3-yl)-propionic acid; or
3-Propyl-3-(4-hydroxy-2-oxo-2H-chromen-3-yl)-propionic acid methyl ester.

5. A compound or salt according to claim 1 that is
3-Propyl-3-(4-hydroxy-2-oxo-2H-chromen-3-yl)-propionic acid ethyl ester;
3-Propyl-3-(4-hydroxy-2-oxo-2H-chromen-3-yl)-propionic acid n-propyl ester;
(4-Hydroxy-2-oxo-2H-chromen-3-yl)-phenyl-acetic acid;
(4-Hydroxy-2-oxo-2H-chromen-3-yl)-phenyl-acetic acid methyl ester; or
(4-Hydroxy-2-oxo-2H-chromen-3-yl)-phenyl-acetic acid ethyl ester.

6. A compound or salt according to claim 1 that is
(4-Hydroxy-2-oxo-2H-chromen-3-yl)-phenyl-acetic acid n -propyl ester;
(4-Hydroxy-2-oxo-2H-chromen-3-yl)-phenyl-acetic acid 2-propyl ester;
(4-Hydroxy-2-oxo-2H-chromen-3-yl)-phenyl-acetic acid n -butyl ester;
2-(4-Hydroxy-2-oxo-2H-chromen-3-yl)-butyric acid;
2-(4-Hydroxy-2-oxo-2H-chromen-3-yl)-butyric acid methyl ester; or 2-(4-Hydroxy-2-oxo-2H-chromen-3-yl)-butyric acid ethyl ester.

7. A compound or salt according to claim 1 that is
2-(4-Hydroxy-2-oxo-2H-chromen-3-yl)-butyric acid n-propyl ester;
2-(4-Hydroxy-2-oxo-2H-chromen-3-yl)-butyric acid iso-propyl ester;
2-(4-Hydroxy-2-oxo-2H-chromen-3-yl)-butyric acid n-butyl ester;
4-(4-Hydroxy-2-oxo-2H-chromen-3-ylmethyl)-benzoic acid;
4-(4-Hydroxy-2-oxo-2H-chromen-3-ylmethyl)-benzoic acid methyl ester; or
4-(4-Hydroxy-2-oxo-2H-chromen-3-ylmethyl)-benzoic acid ethyl ester.

8. A compound or salt according to claim 1 that is
2-(4-Hydroxy-2-oxo-2H-chromen-3-yl)-butyric acid n-propyl ester;
2-(4-Hydroxy-2-oxo-2H-chromen-3-yl)-butyric acid iso-propyl ester;
2-(4-Hydroxy-2-oxo-2H-chromen-3-yl)-butyric acid n-butyl ester;
4-(4-Hydroxy-2-oxo-2H-chromen-3-ylmethyl)-benzoic acid;
4-(4-Hydroxy-2-oxo-2H-chromen-3-ylmethyl)-benzoic acid methyl ester; or
4-(4-Hydroxy-2-oxo-2H-chromen-3-ylmethyl)-benzoic acid ethyl ester.

9. A compound or salt according to claim 1 that is
4-(4-Hydroxy-2-oxo-2H-chromen-3-ylmethyl)-benzoic acid n -propyl ester;
4-(4-Hydroxy-2-oxo-2H-chromen-3-ylmethyl)-benzoic acid n -butyl ester;
2-(4-Hydroxy-2-oxo-2H-chromen-3-ylmethyl)-benzoic acid;
2-(4-Hydroxy-2-oxo-2H-chromen-3-ylmethyl)-benzoic acid methyl ester;
2-(4-Hydroxy-2-oxo-2H-chromen-3-ylmethyl)-benzoic acid ethyl ester;
2-(4-Hydroxy-2-oxo-2H-chromen-3-ylmethyl)-benzoic acid n -propyl ester;
2-(4-Hydroxy-2-oxo-2H-chromen-3-ylmethyl)-benzoic acid n -butyl ester;
3-(4-Hydroxy-2-oxo-2H-chromen-3-ylmethyl)-benzoic acid;
3-(4-Hydroxy-2-oxo-2H-chromen-3-ylmethyl)-benzoic acid methyl ester; or
3-(4-Hydroxy-2-oxo-2H-chromen-3-ylmethyl)-benzoic acid ethyl ester.

10. A compound or salt according to claim 1 that is
3-(4Hydroxy-2-oxo-2H-chromen-3-ylmethyl)-benzoic acid n -propyl ester;
3-(4-Hydroxy-2-oxo-2H-chromen-3-ylmethyl)-benzoic acid n -butyl ester;
2-Benzyl-3-(4-hydroxy-2-oxo-2H-chromen-3-yl)-propionic acid;
2-Benzyl-3-(4-hydroxy-2-oxo-2H-chromen-3-yl)-propionic acid methyl ester;
2-Benzyl-3-(4-hydroxy-2-oxo-2H-chromen-3-yl)-propionic acid ethyl ester;
2-Benzyl-3-(4-hydroxy-2-oxo-2H-chromen-3-yl)-propionic acid n-propyl ester;
2-Benzyl-3-(4-hydroxy-2-oxo-2H-chromen-3-yl)-propionic acid n-butyl ester;
2-(4-Hydroxy-2-oxo-2H-chromen-3-ylmethyl)-butyric acid; or 2-(4-Hydroxy-2-oxo-2H-chromen-3-ylmethyl)-butyric acid methyl ester.

11. A compound or salt according to claim 1 that is
2-(4-Hydroxy-2-oxo-2H-chromen-3-ylmethyl)-butyric acid ethyl ester;
2-(4-Hydroxy-2-oxo-2H-chromen-3-ylmethyl)-butyric acid n-propyl ester;
2-(4-Hydroxy-2-oxo-2H-chromen-3-ylmethyl)-butyric acid n-butyl ester;
4-[(4-Hydroxy-2-oxo-2H-chromen-3-yl)-(4-hydroxy-1-oxo-1H-isochromen-3-yl)-methyl]-benzoic acid methyl ester;
4-[(4-Hydroxy-2-oxo-2H-chromen-3-yl)-(4-hydroxy-1-oxo-1H-isochromen-3-yl)-methyl]-benzoic acid ethyl ester;
4-[(4-Hydroxy-2-oxo-2H-chromen-3-yl)-(4-hydroxy-1-oxo-1H-isochromen-3-yl)-methyl]-benzoic acid n-propyl ester;
4-[(4-Hydroxy-2-oxo-2H-chromen-3-yl)-(4-hydroxy-1-oxo-1H-isochromen-3-yl)-methyl]-benzoic acid n-butyl ester; or
3-[(4-Hydroxy-2-oxo-2H-chromen-3-yl)-(4-hydroxy-1-oxo-1H-isochromen-3-yl)-methyl]-benzoic acid.

12. A compound or salt according to claim 1 that is
3-[(4-Hydroxy-2-oxo-2H-chromen-3-yl)-(4-hydroxy-1-oxo-1H-isochromen-3-yl)-methyl]-benzoic acid methyl ester;
3-[(4-Hydroxy-2-oxo-2H-chromen-3-yl)-(4-hydroxy-1-oxo-1H-isochromen-3-yl)-methyl]-benzoic acid ethyl ester;
3-[(4-Hydroxy-2-oxo-2H-chromen-3-yl)-(4-hydroxy-1-oxo-1H-isochromen-3-yl)-methyl]-benzoic acid n-propyl ester;
3-[(4-Hydroxy-2-oxo-2H-chromen-3-yl)-(4-hydroxy-1-oxo-1H-isochromen-3-yl)-methyl]-benzoic acid n-butyl ester;
2-[(4-Hydroxy-2-oxo-2H-chromen-3-yl)-(4-hydroxy-1-oxo-1H-isochromen-3-yl)-methyl]-benzoic acid;
2-[(4-Hydroxy-2-oxo-2H-chromen-3-yl)-(4-hydroxy-1-oxo-1H-isochromen-3-yl)-methyl]-benzoic acid methyl ester;
2-[(4-Hydroxy-2-oxo-2H-chromen-3-yl)-(4-hydroxy-1-oxo-1H-isochromen-3-yl)-methyl]-benzoic acid ethyl ester;
2-[(4-Hydroxy-2-oxo-2H-chromen-3-yl)-(4-hydroxy-1-oxo-1H-isochromen-3-yl)-methyl]-benzoic acid n-propyl ester; or
2-[(4-Hydroxy-2-oxo-2H-chromen-3-yl)-(4-hydroxy-1-oxo-1H-isochromen-3-yl)-methyl]-benzoic acid n-butyl ester.

* * * * *

UNITED STATES PATENT AND TRADEMARK OFFICE
CERTIFICATE OF CORRECTION

| | | |
|---|---|---|
| PATENT NO. | : 7,145,020 B2 | Page 1 of 1 |
| APPLICATION NO. | : 10/822129 | |
| DATED | : December 5, 2006 | |
| INVENTOR(S) | : Pascal Druzgala, Xiaoming Zhang and Jurg R. Pfister | |

It is certified that error appears in the above-identified patent and that said Letters Patent is hereby corrected as shown below:

Title Page:

Item (75), Inventors, delete "Jurg R. Pfiste, Los Altos, CA (US)" and add -- Jurg R. Pfister, Los Altos, CA (US) --

Signed and Sealed this

Twentieth Day of February, 2007

JON W. DUDAS
*Director of the United States Patent and Trademark Office*